United States Patent
Gomi

(10) Patent No.: US 8,330,948 B2
(45) Date of Patent: Dec. 11, 2012

(54) SEMICONDUCTOR TEST INSTRUMENT AND THE METHOD TO TEST SEMICONDUCTOR

(75) Inventor: Kenji Gomi, Tokyo (JP)

(73) Assignee: Tokyo Denki University, Tokyo (JP)

(*) Notice: Subject to any disclaimer, the term of this patent is extended or adjusted under 35 U.S.C. 154(b) by 264 days.

(21) Appl. No.: 12/712,760

(22) Filed: Feb. 25, 2010

(65) Prior Publication Data

US 2010/0271633 A1    Oct. 28, 2010

(30) Foreign Application Priority Data

Apr. 24, 2009   (JP) ................. 2009-106852

(51) Int. Cl.
  *G01N 21/00* (2006.01)
(52) U.S. Cl. ............. 356/237.2; 356/237.1; 356/237.6
(58) Field of Classification Search ..... 356/237.2–237.6
  See application file for complete search history.

(56) References Cited

U.S. PATENT DOCUMENTS

| | | | | |
|---|---|---|---|---|
| 5,367,174 A | * | 11/1994 | Bazile et al. ............. | 250/559.45 |
| 6,433,867 B1 | * | 8/2002 | Esquivel .................. | 356/237.2 |
| 7,847,237 B2 | * | 12/2010 | Fuyuki ..................... | 250/238 |
| 2005/0252545 A1 | * | 11/2005 | Nowlan et al. ............ | 136/290 |
| 2008/0213926 A1 | * | 9/2008 | Tajima et al. ............. | 438/16 |

FOREIGN PATENT DOCUMENTS

JP   2008-026113   2/2008

* cited by examiner

*Primary Examiner* — Tarifur Chowdhury
*Assistant Examiner* — Isiaka Akanbi
(74) *Attorney, Agent, or Firm* — Maschoff Gilmore & Israelsen

(57) ABSTRACT

A semiconductor examination apparatus includes an energy source device that supplies a semiconductor substrate having a pn junction with excitation energy that causes luminescence in the semiconductor substrate, an image capturing device that captures a first luminescence image of the semiconductor substrate supplied with first excitation energy and a second luminescence image of the semiconductor substrate supplied with second excitation energy that is different in magnitude from the first excitation energy, a luminescence image processing device that calculates the difference in luminescence intensity between the first luminescence image and the second luminescence image at positions on the semiconductor substrate and generates intensity difference image data, and a detecting device that detects a crack position of a crack occurring in the semiconductor substrate on the basis of determination values based on the magnitude of the difference on the intensity difference image data.

20 Claims, 14 Drawing Sheets

US 8,330,948 B2

SEMICONDUCTOR TEST INSTRUMENT AND THE METHOD TO TEST SEMICONDUCTOR

CROSS-REFERENCE TO RELATED APPLICATIONS

This application claims priority to Japanese Patent Application No. 2009-106852, filed Apr. 24, 2009, which is incorporated herein by reference.

TECHNICAL FIELD

A semiconductor apparatus and semiconductor examination method that detect a crack in a semiconductor substrate.

BACKGROUND

The intensity of luminescence occurring in a semiconductor substrate is substantially proportional to the excitation energy supplied to the semiconductor substrate. However, luminescence may not be observed on a crack in a semiconductor substrate, while the diffraction of ambient luminescence may only be observed at the crack.

There has been proposed in Japanese Unexamined Patent Application Publication No. 2008-26113 a method of photographing an image of a semiconductor substrate in the state where luminescence is caused (hereinafter called a "luminescence image") and detecting a crack on the semiconductor substrate.

However, the detection of a crack using the luminescence image often requires the use of a high-performance camera that is capable of capturing an image that clearly shows the difference between a position of the substrate with a crack and a position of the substrate without a crack. This may increase the price of an examination apparatus for detecting a crack with high precision that uses the luminescence image. Furthermore, the export of examination apparatuses containing a high-performance camera may be restricted.

SUMMARY

Accordingly, it would be advantageous to provide an inexpensive semiconductor examination apparatus and semiconductor examination method that can detect a crack in a semiconductor substrate with high precision using a luminescence image of the semiconductor substrate.

In one embodiment, there is provided a semiconductor examination apparatus. The semiconductor examination apparatus includes an energy source device that supplies a semiconductor substrate having a pn junction with excitation energy to cause luminescence in the semiconductor substrate, an image capturing device that captures a first luminescence image of the semiconductor substrate when the semiconductor substrate is supplied with first excitation energy and captures a second luminescence image of the semiconductor substrate when the semiconductor substrate is supplied with second excitation energy that is different in magnitude from the first excitation energy, a luminescence image processing device that calculates the difference in luminescence intensity between the first luminescence image and the second luminescence image at corresponding positions on the semiconductor substrate and generates intensity difference image data, and a detecting device that detects a crack position of a crack occurring in the semiconductor substrate on the basis of determination values that are based on the magnitude of the difference on the intensity difference image data.

In another embodiment, there is provided a semiconductor examination method. The semiconductor examination method includes the steps of supplying first excitation energy to a semiconductor substrate having a pn junction and acquiring a first luminescence image of the semiconductor substrate, supplying second excitation energy that is different in magnitude from the first excitation energy to the semiconductor substrate and acquiring a second luminescence image of the semiconductor substrate, calculating the difference in luminescence intensity between the first luminescence image and the second luminescence image at positions on the semiconductor substrate and generating intensity difference image data, and detecting a crack position of a crack occurring in the semiconductor substrate on the basis of determination values that are based on the magnitude of the difference on the intensity difference image data.

DETAILED DESCRIPTION

With reference to drawings, first and second embodiments will be described herein. Identical or similar symbols refer to identical or similar parts on drawings, which are described below. The first and second embodiments are only for the purpose of illustration of an apparatus or method embodying the technical spirit of the embodiments disclosed herein. The technical spirit including the structures and arrangements of the components of the embodiments disclosed herein is not specified by those described below. Various changes can be made to the embodiments disclosed herein without departing from the scope of the present technological advancement.

Figure 1:
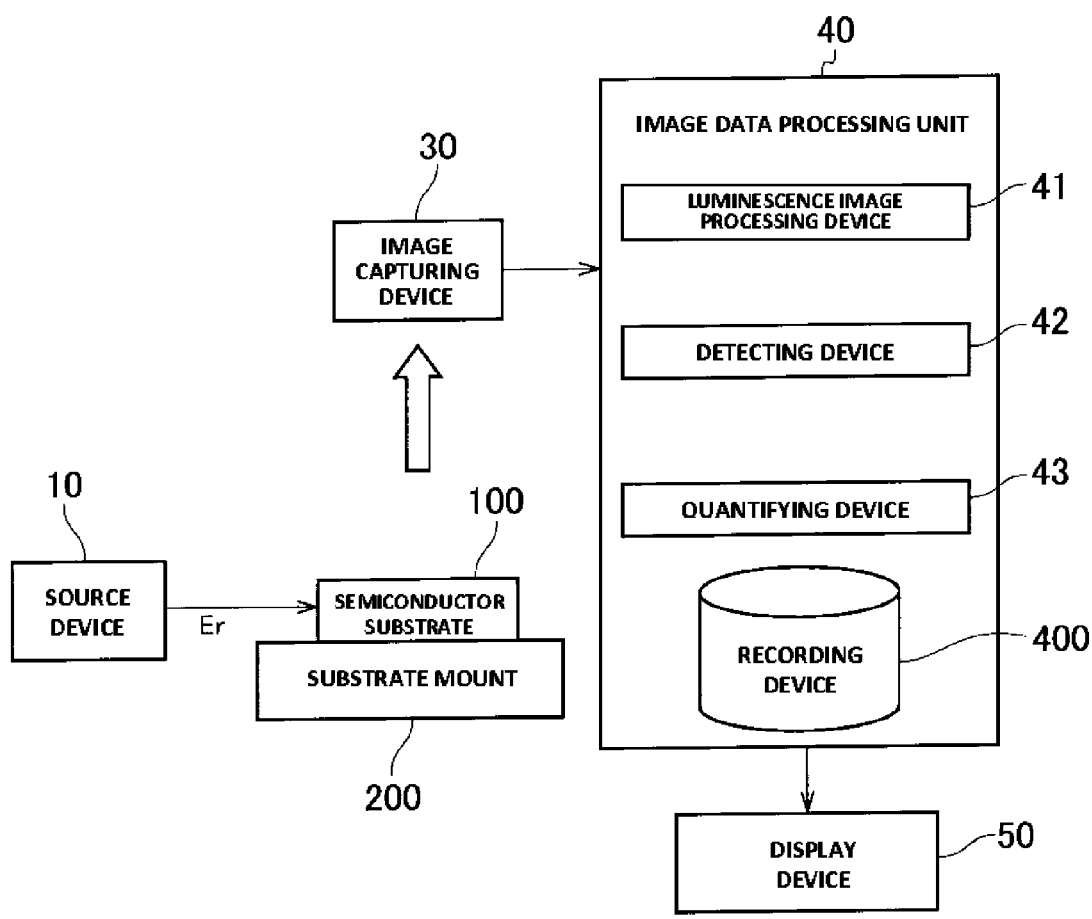
FIG. 1 is a schematic diagram illustrating a configuration of a semiconductor examination apparatus according to a first embodiment.

A semiconductor examination apparatus according to the first embodiment includes, as illustrated in FIG. 1, an energy source device 10. The energy source device 10 supplies a semiconductor substrate 100 having a pn junction with excitation energy Er that causes luminescence in the semiconductor substrate. The semiconductor examination apparatus also includes an image capturing device 30. The imaging capturing device 30 captures a first luminescence image of the semiconductor substrate 100 when the semiconductor substrate 100 is supplied with first excitation energy Er1 and captures a second luminescence image of the semiconductor substrate 100 when the semiconductor substrate 100 is supplied with second excitation energy Er2 that is different in magnitude from the first excitation energy Er1.

The semiconductor examination apparatus further includes a luminescence image processing device 41. The luminescence image processing device 41 calculates the difference in luminescence intensity between the first luminescence image and the second luminescence image at corresponding positions on the semiconductor substrate 100 and generates intensity difference image data.

The semiconductor examination apparatus additionally includes a detecting device 42. The detecting device 42 detects a crack position of a crack occurring in the semiconductor substrate 100 on the basis of determination values that are based on the magnitude of the difference on the intensity difference image data.

The data on the image captured by the image capturing device 30 is transmitted to the image data processing unit 40 having the luminescence image processing device 41 and detecting device 42. The image data processing unit 40 further includes a quantifying device 43 that quantifies the volume of the crack with the number of pixels having a crack. The quantifying device 43 counts the number of pixels contained in a crack position and calculates a total sum of the counted number of pixels as the volume of the crack. The data processed by the image data processing unit 40 is stored in the recording device 400.

The energy source device 10 is an output-adjustable energy source that can supply different magnitudes of the excitation energy Er to the semiconductor substrate 100. For example, the energy source device 10 may apply current or voltage to supply the excitation energy Er to the semiconductor substrate 100. In this case, by changing the magnitude of current or voltage to be applied, the energy source device 10 can supply the excitation energy Er having different magnitudes to the semiconductor substrate 100. Since the intensity of the luminescence caused in the semiconductor substrate 100 is substantially proportional to the supplied excitation energy Er, the energy source device 10 can cause luminescence having a variety of intensities in the semiconductor substrate 100.

Typically, a semiconductor substrate includes a semiconductor area having a pn junction where luminescence may be caused by the supply of the excitation energy Er and the area excluding the semiconductor area but including wiring of electrodes (called an "electrode wire" hereinafter). In general, luminescence is not caused in the area excluding the semiconductor area even when supplied by the excitation energy Er. Hereinafter, the area where luminescence is not caused even when supplied by the excitation energy Er under a normal state will be called a "non-EL area". When the excitation energy Er is supplied to the semiconductor substrate 100 having a crack, luminescence is not caused in the crack and the non-EL area. Thus, the pn junction area (hereinafter called a "normal pn junction area") without a crack in the semiconductor area has a higher luminescence intensity while the crack and non-EL area have a lower luminescence intensity.

The image capturing device 30 images a luminescence image of the semiconductor substrate 100 where luminescence has been caused by the supply of the excitation energy Er and acquires the data as image data. More specifically, the image capturing device 30 acquires luminescence images having different luminescence intensities of the normal pn junction area, the crack position, and the non-EL area and transmits the acquired luminescence images to the image data processing unit 40. In order to image the luminescence images, an infrared camera, for example, may be used as the image capturing device 30. The image capturing device 30 may be an inexpensive imaging apparatus such as a charge-coupled device (CCD) camera.

On the basis of the luminescence images acquired by the image capturing device 30, the luminescence image processing device 41 creates intensity difference image data having a correspondence between luminescence intensities and positions within the semiconductor substrate 100.

For example, when luminance distributions are acquired as the luminescence images, the luminescence image processing device 41 creates luminance-distribution image data as the intensity difference image data. On the semiconductor substrate 100 where luminescence has been caused by the supply of the excitation energy Er, no luminescence is observed at a position having a crack. This allows for distinction between a crack and the normal pn junction area in the intensity difference image data.

However, the distinction between a crack and a normal pn junction area may be significantly difficult unless an expensive camera having high performance is used as the image capturing device 30, for example. In order to allow the distinction between a crack and a normal pn junction area with the image capturing device 30 having low performance, the semiconductor examination apparatus illustrated in FIG. 1 creates the intensity difference image data on the basis of the difference in intensity between two luminescence images, as will be described below.

As already described, the luminescence intensity of the semiconductor substrate 100 is substantially proportional to the magnitude of the supplied excitation energy Er. Thus, when the excitation energies Er having different magnitudes are supplied to the semiconductor substrate 100, the intensities of luminescence in the area where luminescence is caused differs in accordance with the magnitude of the excitation energy Er. On the other hand, the intensities of luminescence in the area where luminescence is not caused does not differ largely.

Therefore, the intensity difference image data is created as follows. First excitation energy Er1 is supplied to the semiconductor substrate 100 and a first luminescence image is acquired. Second excitation energy Er2 having a different magnitude from that of the first excitation energy Er1 is supplied to the semiconductor substrate 100 and a second luminescence image having a different luminescence intensity from that of the first luminescence image is acquired. The luminescence image processing device 41 calculates the differences in luminescence intensity between the first luminescence image and the second luminescence image at corresponding positions of the semiconductor substrate 100 and creates an intensity difference image data therefrom. In the intensity difference image data, the area where luminescence is not caused has a difference in luminescence intensity smaller than the difference in luminescence intensity in the normal pn junction area.

For example, if the luminescence image is a luminance distribution image, the luminance of the semiconductor substrate 100 where luminescence has been caused is substantially proportional to the magnitude of the supplied excitation energy Er. Thus, the difference in luminance in the normal pn junction area of the first luminescence image and the second luminescence image is larger than the difference in luminance of a crack position. This can emphasize the darkness of the crack position and the non-EL area of the intensity difference image data acquired based on the calculated result of the difference between the first luminescence image and the second luminescence image. In other words, the darkness of a crack position is more emphasized than the normal pn junction area.

Figure 2:
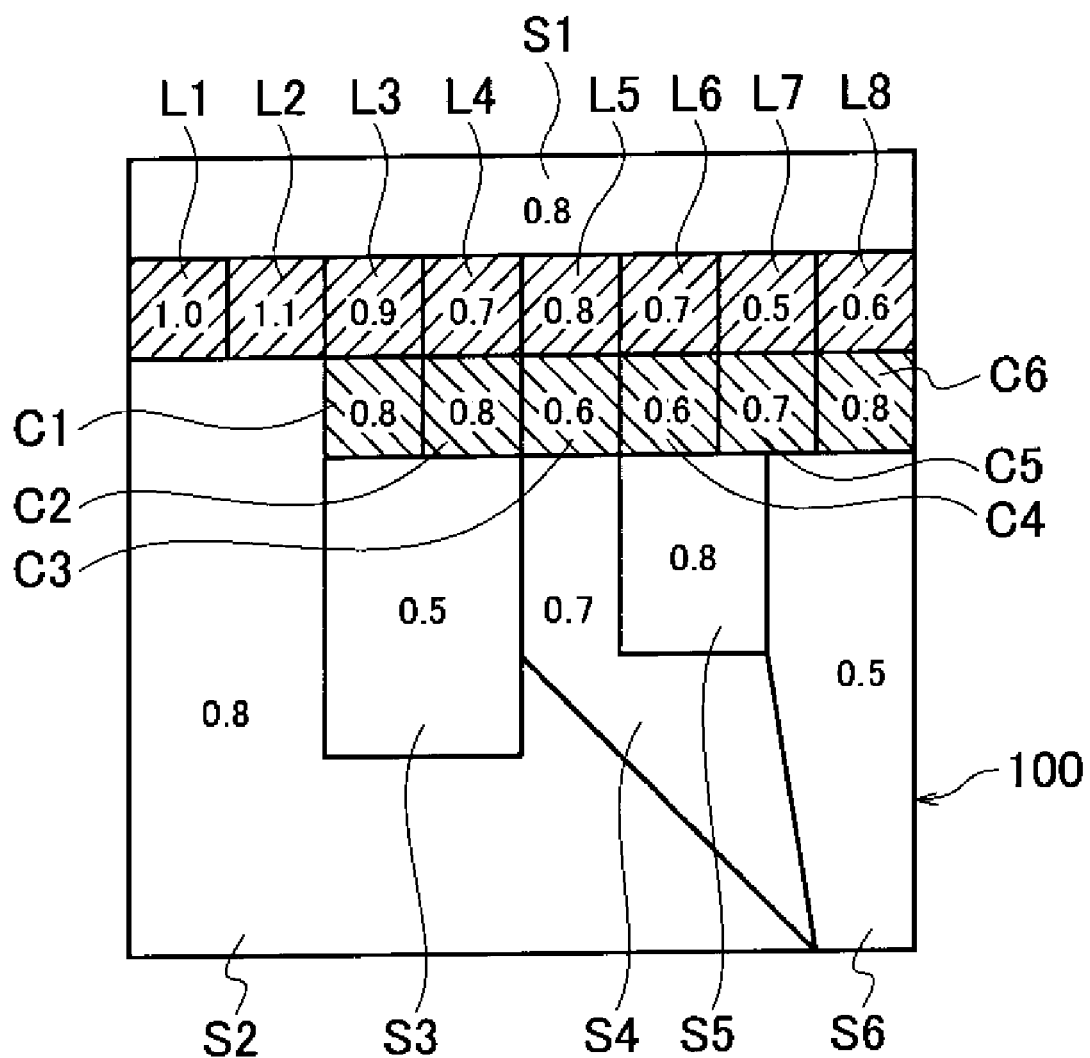
FIG. 2 is a schematic diagram illustrating an example of a luminescence image acquired by a semiconductor examination apparatus according to the first embodiment.

FIG. 2 illustrates an example of the luminance distribution image of a surface of the semiconductor substrate 100 acquired as the first luminescence image. In FIG. 2, normal pn junction areas S1 to S6 are not shaded. Non-EL areas L1 to L8 having an electrode wire, for example, are shaded with inclined lines. Crack positions C1 to C6 having a crack are shaded with declined lines. The numbers at the centers of the illustrated areas indicate the corresponding luminances.

The luminance distribution image illustrated in FIG. 2 is an example of the image in the case where crack detection is difficult because the crack positions and the electrode wire are neighboring each other and the differences in luminance between the normal pn junction areas S1 to S6, non-EL areas L1 to L8, and crack positions C1 to C6 are small. When the image capturing device 30 has low performance, a luminance distribution image is acquired which has little difference in luminance between the normal pn junction areas S1 to S6, non-EL areas L1 to L8, and crack positions C1 to C6, as illustrated in FIG. 2.

Figure 3:
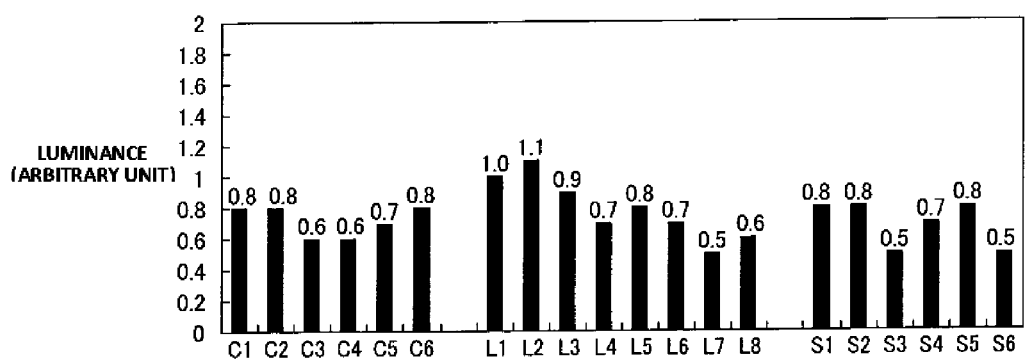
FIG. 3 is a graph illustrating a luminance distribution of the luminescence image illustrated in FIG. 2.

FIG. 3 illustrates a luminance distribution (hereinafter, called a "first luminance distribution") of the luminance distribution image illustrated in FIG. 2 which is acquired as the first luminescence image. FIG. 3 is a graph illustrating luminances at corresponding positions (and the same is true hereinafter). The detection of a crack position is difficult from the luminance distribution having small differences in luminance between the normal pn junction areas S1 to S6 and the crack positions C1 to C6 as illustrated in FIG. 3.

Figure 4:
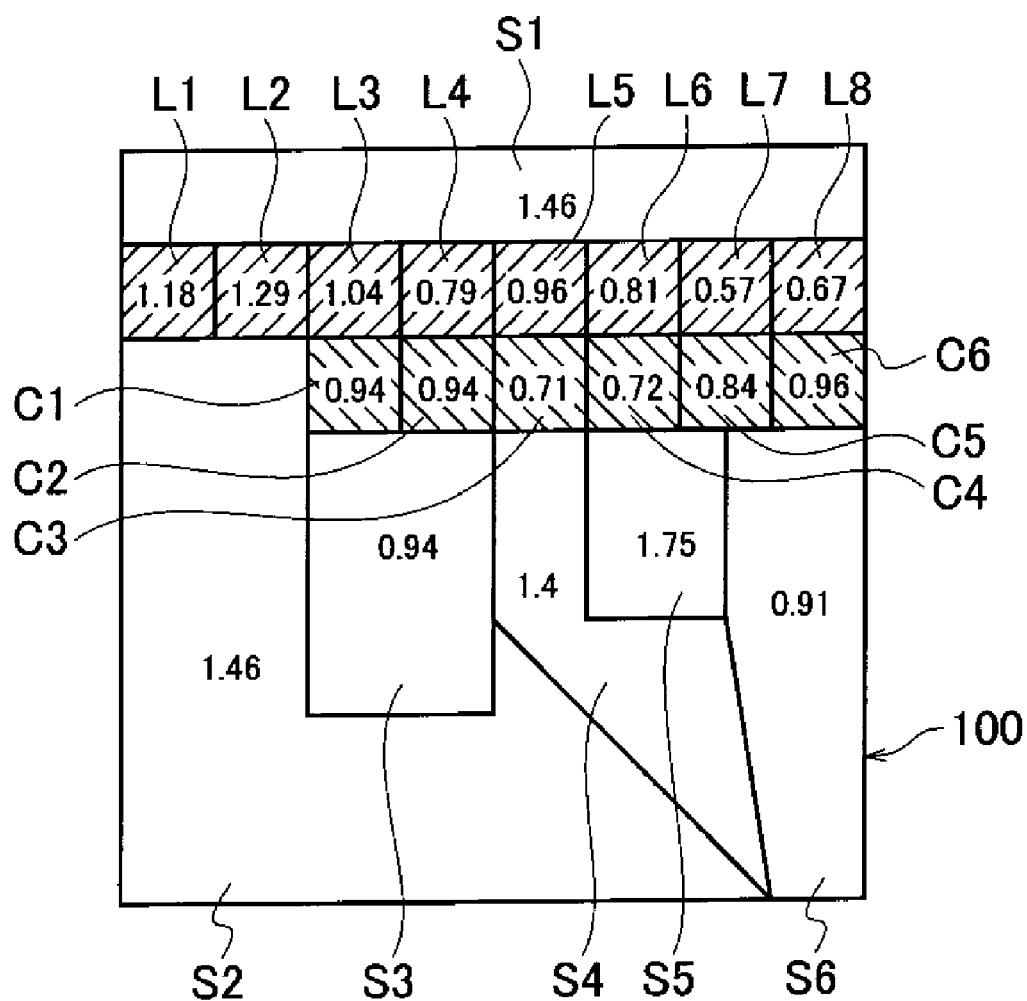
FIG. 4 is a schematic diagram illustrating another example of a luminescence image acquired by a semiconductor examination apparatus according to the first embodiment.

FIG. 4 illustrates an example of a luminance distribution image acquired as a second luminescence image. The second luminescence image is a luminance distribution image which is acquired by the supply, to the semiconductor substrate 100, of the excitation energy Er having the double magnitude of that of the excitation energy Er supplied to semiconductor substrate 100 to acquire the first luminescence image. When the image capturing device 30 has low performance, noise may lower the luminance of the acquired image data and it is difficult to precisely recognize the change in intensity of the luminescence image with the excitation energy Er having the double magnitude. For that, as illustrated in FIG. 4, the luminance of the second luminescence image in the normal pn junction areas do not double the luminance of the first luminescence image.

Figure 5:
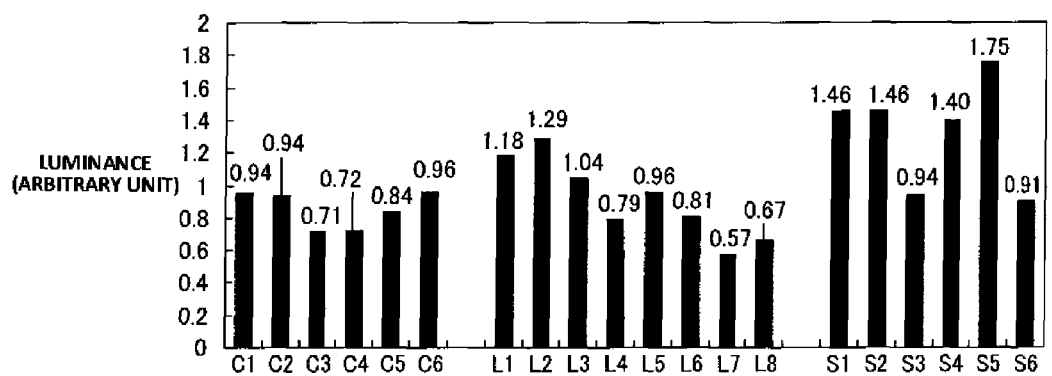
FIG. 5 is a graph illustrating a luminance distribution of the luminescence image illustrated in FIG. 4.

FIG. 5 illustrates a luminance distribution (hereinafter called a "second luminance distribution") of the luminance distribution image illustrated in FIG. 4. The luminance distribution illustrated in FIG. 5 has small differences in luminance between the normal pn junction areas S1 to S6 and the crack positions C1 to C6. Thus, the detection of crack positions is difficult.

Figure 6:
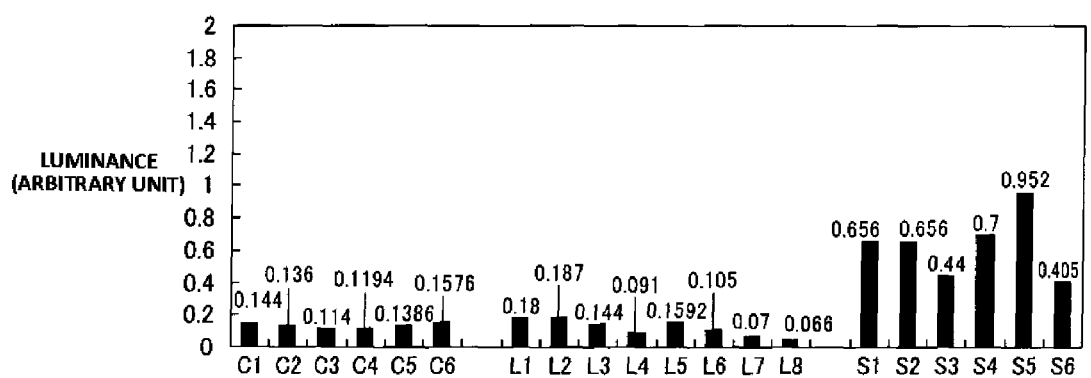
FIG. 6 is a graph illustrating an example of a luminance distribution of intensity difference image data created by a semiconductor examination apparatus according to the first embodiment.

When the first luminescence image and second luminescence image are luminance distribution images, the luminescence image processing device 41 creates luminance distribution image data as the intensity difference image data. FIG. 6 illustrates an example of a luminance distribution of the luminance distribution image data created as the intensity difference image data. In other words, FIG. 6 illustrates differences in luminance between the first luminance distribution illustrated in FIG. 3 and the second luminance distribution illustrated in FIG. 5.

As illustrated in FIGS. 3 and 5, the first luminance distribution and the second luminance distribution have small differences in luminance between the normal pn junction areas S1 to S6 and the crack positions C1 to C6. However, as illustrated in FIG. 6, the differences between the first luminance distribution and second luminance distribution emphasize the darker part excluding the normal pn junction areas S1 to S6. This can clarify the differences in luminance between the normal pn junction areas S1 to S6 and the crack positions C1 to C6.

As described above, the difference between luminescence images having different intensities can more clearly clarify a crack position from which no luminescence is observed in the intensity difference image data. The creation of the intensity difference image data by using the difference between the luminescence images may require two luminescence images having different intensities at same positions of the semiconductor substrate 100.

As described above, the intensity difference image data have a clear difference in luminescence intensity between a normal pn junction area and a crack position. Thus, the detecting device 42 may use the magnitude of the difference in the intensity difference image data at the corresponding positions of the semiconductor substrate 100 as the determination values to distinguish between the normal pn junction area of the semiconductor substrate 100 and the semiconductor area having a crack. In other words, the detecting device 42 detects a semiconductor area having a small difference in luminescence intensity as a crack position.

Figure 7:
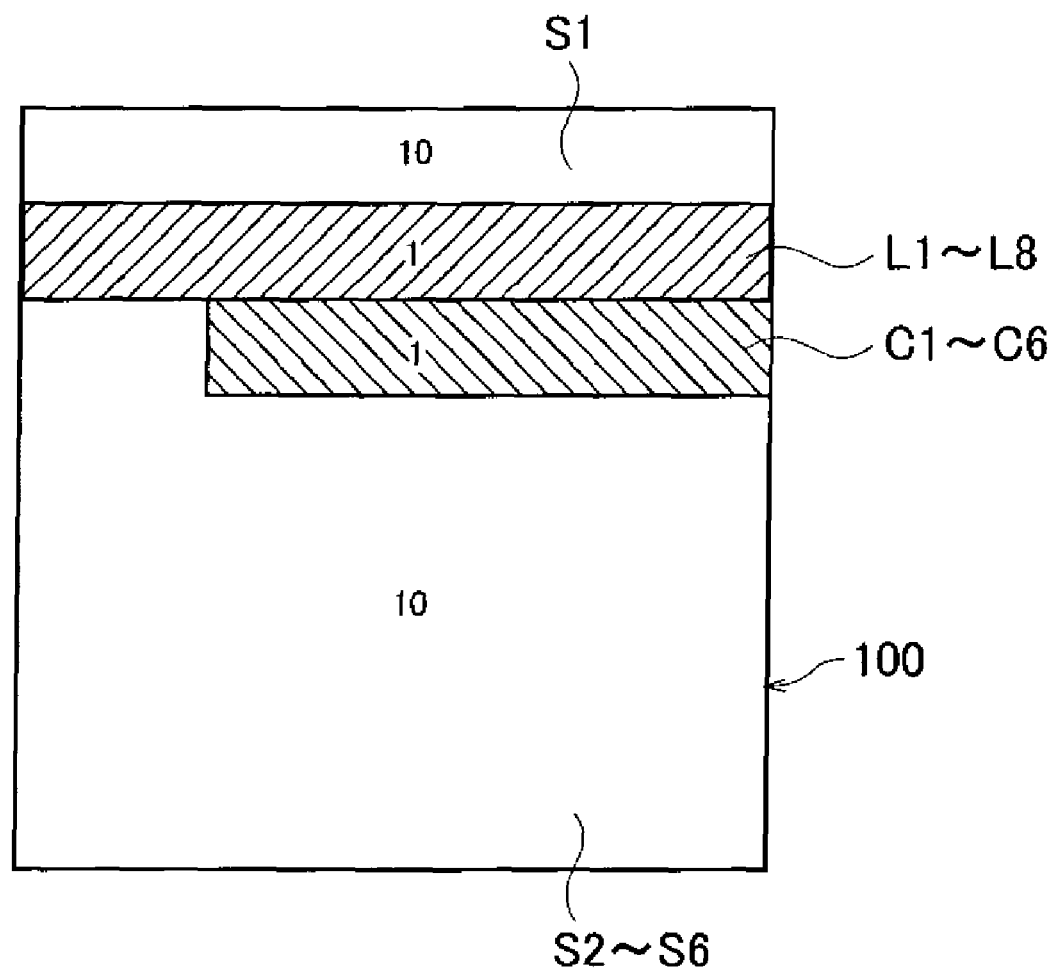
FIG. 7 is a schematic diagram illustrating an example of a determination value distribution image created by a semiconductor examination apparatus according to the first embodiment.

Since the difference is large regarding the difference in a normal pn junction area and a crack position, the difference can be binarized. On the basis of the determination values that are the binarized magnitudes of the difference between the intensity difference image data, a crack position can be detected more easily. FIG. 7 illustrates an example of a determination value distribution image resulting from the binarization of the determination value illustrated in FIG. 6. In FIG. 7, the ratio "value of a normal pn junction area:value of the area excluding the normal pn junction area" is defined as 10:1 for binarization of the determination values.

An examination result by a semiconductor examination apparatus according to the first embodiment is displayed on the display device 50. For example, the position and/or length where a crack is detected may be displayed on the display device 50. The volume of the crack calculated by the quantifying device 43 may also be displayed on the display device 50.

The semiconductor substrate 100 that is to be examined is arranged on a substrate mount 200. The substrate mount 200 is controlled to move the semiconductor substrate 100 to an arbitrary position within a range of imaging by the image capturing device 30. For example, when the semiconductor substrate 100 is too large to fit into the range of imaging by the image capturing device 30, the semiconductor substrate 100 may be moved to photograph a number of images. Those images may be synthesized to acquire the composite image data on the semiconductor substrate 100. The arrangement of a number of semiconductor substrates 100 on the substrate mount 200 may allow serial examination of the number of semiconductor substrates 100.

The image capturing device 30 may be only required to have enough performance for photographing a luminescence image. For example, an infrared camera that is sensitive to a wavelength band 1000 nm to 1300 nm may be used to photograph a luminescence image. Preferably, the image capturing device 30 can photograph luminescence images from which an approximately twice luminance change can be identified in order to calculate the difference in intensity between a first luminescence image and a second luminescence image. However, a low-performance camera allowing the identification of an approximately twice luminance change as a luminance change of 1.5 times may be used as the image capturing device 30. This is because, with the supply of the excitation energy Er having a triple magnitude, such a low-performance camera can acquire a luminance distribution equivalent to that by a high-performance camera having high fidelity.

Thus, even a low-performance camera, instead of an expensive high-performance camera, can satisfy the requirements of the image capturing device 30. In other words, an inexpensive camera may be used as the image capturing device 30 to acquire the luminance distribution images as illustrated in FIGS. 2 to 6 and to detect a crack position as described above.

In this way, a semiconductor examination apparatus according to the first embodiment calculates the difference in luminescence intensity between two luminescence images having different intensities to create intensity difference image data having a large difference between a crack position from which luminescence is not observed and a normal pn junction area. The magnitudes of the differences in the intensity difference image data may be used as the determination values to detect a crack position in a semiconductor area. As a result, the semiconductor examination apparatus illustrated in FIG. 1 can implement an inexpensive semiconductor examination apparatus that can detect the positions and/or length of a crack in the semiconductor substrate 100 with high precision using the luminescence images. Furthermore, the semiconductor examination apparatus illustrated in FIG. 1 can quantify the volume of the crack by using the number of pixels having a crack. Thus, for example, the quantified volume of the crack may be used to classify the quality of the semiconductor substrate 100 into several levels.

Figure 8:
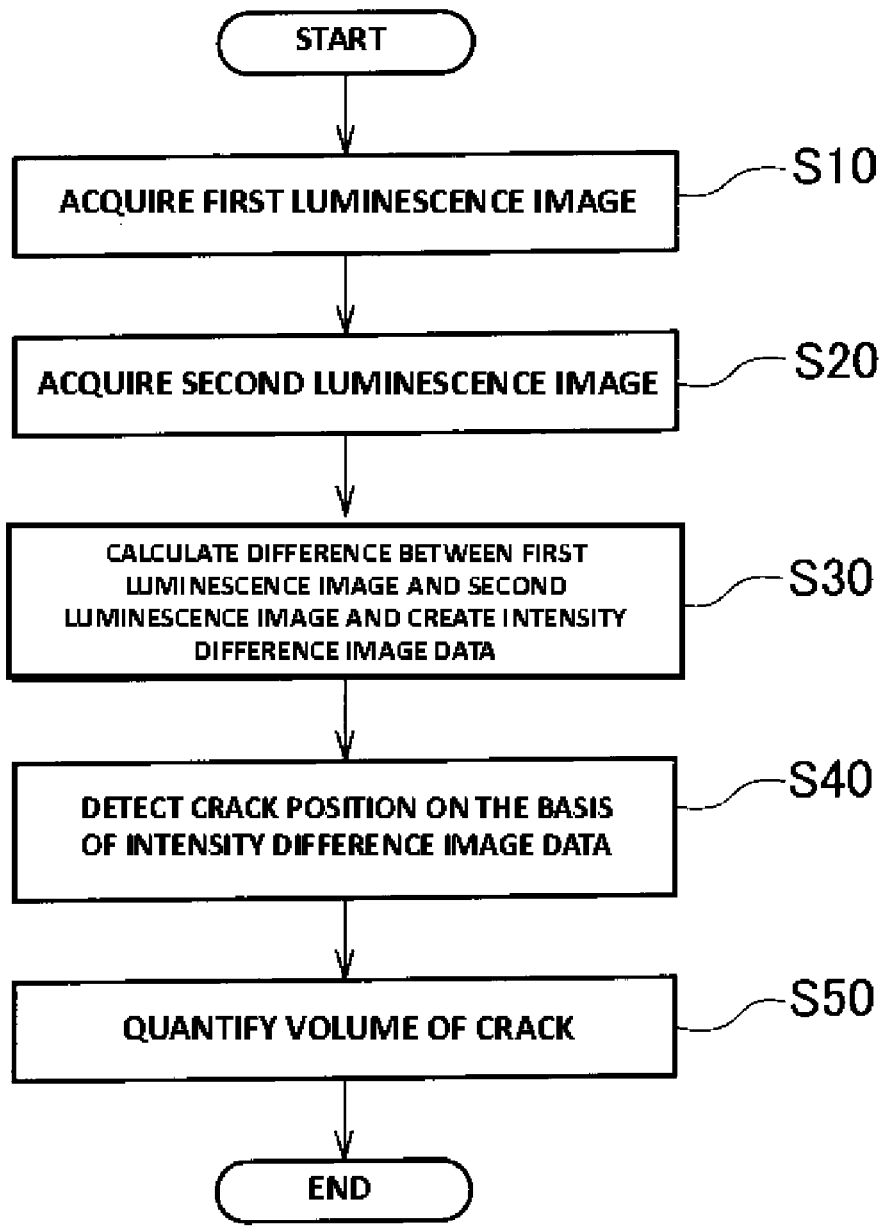
FIG. 8 is a flowchart illustrating a semiconductor examination method according to the first embodiment.

Reference is made to the flowchart in FIG. 8 to describe a method that uses the semiconductor examination apparatus illustrated in FIG. 1 to exam the semiconductor substrate 100. The semiconductor substrate 100 may be any semiconductor substrate where the supply of excitation energy causes luminescence. An example in which the semiconductor substrate 100 is a solar cell substrate will be described below. In the example, the non-EL area corresponds to an area including an electrode wire.

In step S10, first excitation energy Er1 that causes luminescence in the semiconductor substrate 100 is supplied from the energy source device 10 to the semiconductor substrate 100. The image capturing device 30 then acquires a first luminescence image of the semiconductor substrate 100. The acquired first luminescence image is transmitted to the image data processing unit 40 and is stored as two-dimensional array data in the recording device 400.

For example, a voltage V1 is applied to an output electrode of a solar cell substrate and causes electroluminescence (EL) in the solar cell substrate. The image capturing device 30 may acquire a luminance distribution image of the solar cell substrate where EL has caused the first luminescence image. For example, a luminance distribution image as illustrated in FIG. 2 may be acquired as the first luminescence image.

In step S20, second excitation energy Er2 having a different magnitude from that of the first excitation energy Er1 is supplied from the energy source device 10 to the semiconductor substrate 100. The image capturing device 30 acquires a second luminescence image of the semiconductor substrate 100 that has a different intensity from that of the first luminescence image. The acquired second luminescence image is transmitted to the image data processing unit 40 and is stored as two-dimensional array data in the recording device 400. For example, a voltage V2 having a double magnitude of the voltage V1 is applied to an output electrode of the solar cell substrate and causes electroluminescence (EL) in the solar cell substrate. The image capturing device 30 acquires a luminance distribution of the solar cell substrate where EL has caused the second luminescence image having a different luminance from that of the first luminescence image. For example, a luminance distribution image as illustrated in FIG. 4 may be acquired as the second luminescence image. It is noted here that a luminance distribution at the same positions as the positions where the first luminescence image has been acquired is acquired as the second luminescence image.

In step S30, the luminescence image processing device 41 calculates differences in intensity at the same positions between the first luminescence image and the second luminescence image and thus creates the intensity difference image data of the semiconductor substrate 100. The created intensity difference image data is stored in the recording device 400. For example, when luminance distribution images are acquired as the first luminescence image and second luminescence image of a solar cell substrate, the luminance distribution image having a luminance distribution as illustrated in FIG. 6 is created as the intensity difference image data.

In step S40, the detecting device 42 uses the intensity difference image data read from the recording device 400 as the determination values to detect a crack position where a crack occurs in the semiconductor area of the semiconductor substrate 100. Here, the data containing the binarized determination values may be referred to and the crack position is detected. The data on the detected crack position is stored in the recording device 400. For example, the luminance distribution illustrated in FIG. 6 may be referred to and a position having a low luminance is detected as the crack position where a crack has occurred.

In step S50, the quantifying device 43 reads the data on the crack position from the recording device 400. The quantifying device 43 counts the number of pixels contained in the crack position and quantifies the total sum of the number of pixels as the volume of the crack. The volume of the crack is stored in the recording device 400.

An operator of the semiconductor examination apparatus may read and display on the display device 50 the data on the determination value and/or crack position stored in the recording device 400. For example, the differences in luminance illustrated in FIG. 6 may be binarized, and a determination value distribution image as illustrated in FIG. 7 may be displayed on the display device 50. Thus, the operator can easily check the crack position.

The quantified volume of the crack may also be displayed on the display device 50. Thus, for example, the quality of the semiconductor substrate 100 may be classified into some levels in accordance with the quantified volumes of the cracks.

As described above, with the semiconductor examination method using a semiconductor examination apparatus according to the first embodiment, luminescence intensity distribution image data may be calculated to acquire determination values for identification of a crack position at the corresponding positions of the semiconductor substrate 100. As a result, an inexpensive semiconductor examination method can be implemented that can detect the position and/or length of an occurring crack with high precision using luminescence images of the semiconductor substrate 100.

Figure 9:
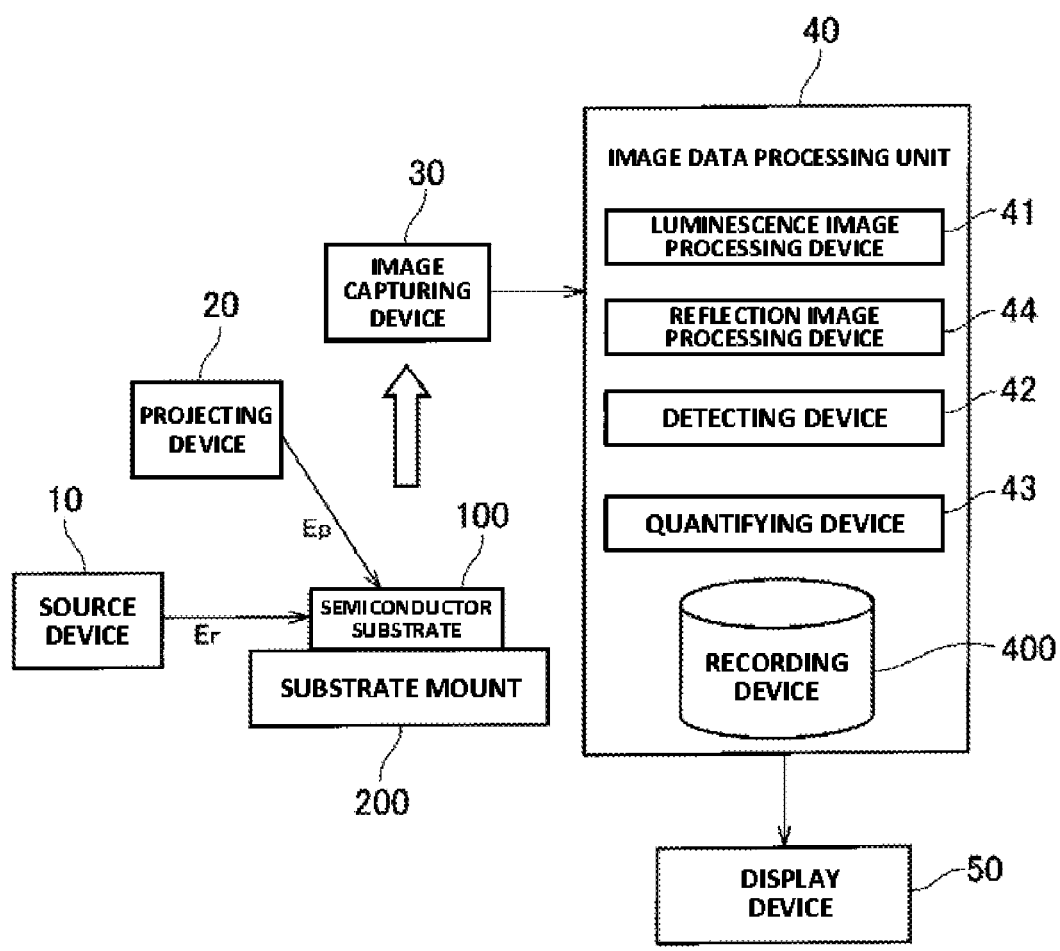
FIG. 9 is a schematic diagram illustrating a configuration of a semiconductor examination apparatus according to a second embodiment.

A semiconductor examination apparatus according to a second embodiment is different from the first embodiment of the semiconductor examination apparatus illustrated in FIG. 1 in that the second embodiment of the semiconductor examination apparatus further includes a projecting device 20 and a reflection image processing device 44, as illustrated in FIG. 9. The other configuration is similar to that of the first embodiment illustrated in FIG. 1.

The projecting device 20 projects to the semiconductor substrate 100 projection energy Ep to be absorbed or reflected at different ratios by a semiconductor area and the area excluding the semiconductor area, where luminescence is not caused, of the semiconductor substrate 100. The reflection image processing device 44 that is included in the image data processing unit 40 binarizes a reflection image of the semiconductor substrate 100 which is acquired with the projection of the projection energy EP to the semiconductor substrate 100 and thus creates the binarized reflection image data.

According to the first embodiment, the semiconductor examination apparatus illustrated in FIG. 1 creates intensity difference image data having a clear difference between a normal pn junction area and a crack position where luminescence is not caused in the semiconductor area.

However, luminescence is not caused in a crack position and not caused in a non-EL area including an electrode wire, for example. Thus, like the intensity difference image data illustrated in FIG. 6, non-EL areas L1 to L8 and crack positions C1 to C6 have small differences in luminance. Therefore, it may be difficult to distinguish between a crack position and a non-EL area on the intensity difference image data.

The projecting device 20 projects the projection energy Ep to the semiconductor substrate 100 in order to distinguish a crack position and a non-EL area. For example, an electrode wire that is in a non-EL area contains a metal film or the like and thus has an optical reflectivity higher than that in the semiconductor area including the position having a crack. Thus, the luminance of light reflected from the electrode wire is higher than the luminance of light reflected from the area excluding the electrode wire. Therefore, the luminances of the reflected light may be used to distinguish between the semiconductor area and the electrode wire.

Accordingly, light can be used as the projection energy Ep to be absorbed or reflected at different ratios in the semiconductor area and non-EL area excluding the semiconductor area, where luminescence is not caused, in the semiconductor substrate 100. Then, a floodlight may be used as the projecting device 20. The reflection image of light reflected by the semiconductor substrate 100 with the projection of light to the semiconductor substrate 100 is a luminance distribution image on which the luminance of the electrode wire is higher than that of the semiconductor area.

As described above, a reflection image on which a semiconductor area and a non-EL area are distinguishable can be acquired with the projection of the projection energy Ep to be absorbed or reflected at different ratios by a semiconductor area and a non-EL area of the semiconductor substrate 100. For example, the difference in luminance on the reflection image allows the distinction between an electrode wire and the area excluding the electrode wire.

Instead of a floodlight, a heater, for example, may be used as the projecting device 20. In this case, the difference in temperature between the heated semiconductor area and electrode wire may be used to acquire a reflection image corresponding to a temperature distribution of the semiconductor substrate 100, where the temperature of the electrode wire is higher. Such a reflection image may be acquired by the use of an infrared camera as the image capturing device 30.

The reflection image processing device 44 binarizes data on the reflection image and creates binarized reflection image data having correspondence between the binarized data and positions within the semiconductor substrate 100. For example, when light is projected as the projection energy Ep to the semiconductor substrate 100, the projecting device 20 acquires a luminance distribution image of light reflected by the semiconductor substrate 100 as the reflection image. The reflection image processing device 44 binarizes the luminances of the luminance distribution image about a predetermined threshold value, for example, and creates luminance distribution image data as the binarized reflection image data.

Typically, a crack is narrower than an electrode wire. Thus, the position of the electrode wire is clear on the reflection image. Therefore, the projection of the projection energy Ep to the semiconductor substrate 100 can provide the reflection image in which a non-EL area having an electrode wire and a semiconductor area excluding the electrode wire are distinguishable. Furthermore, the binarized data of the reflection image allows a clear distinction between the electrode wire arranged on the semiconductor substrate 100 and the area excluding the electrode wire. For example, the ratio "data on the non-EL area: data on the area excluding the non-EL area" may be defined as "10:1" to create the binarized reflection image data. Here, the data on the area excluding an electrode wire is data on the semiconductor area.

Figure 10:
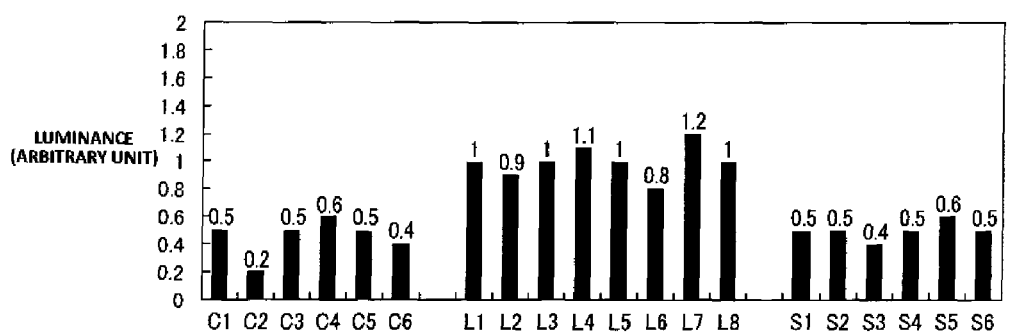
FIG. 10 is a graph illustrating an example of a luminance distribution of a reflection image acquired by a semiconductor examination apparatus according to the second embodiment.

An example will now be described in which light is projected to the semiconductor substrate 100 illustrated in FIG. 2 to acquire the luminance distribution image of light reflected by the semiconductor substrate 100 as the reflection image. FIG. 10 illustrates an example of a luminance distribution of the luminance distribution image acquired as the reflection image. As illustrated in FIG. 10, a large difference in luminance is observed between the normal pn junction areas S1 to S6 and crack positions C1 to C6, and the non-EL areas L1 to L8 having an electrode wire. Thus, even when an inexpensive and low-performance camera is used as the image capturing device 30, the reflection image can be acquired which has a clear difference between a non-EL area and the area excluding the non-EL area.

When the reflection image is a luminance distribution image, the luminance distribution image data is the binarized reflection image data created by the binarization on the reflection image. When the non-EL area has an electrode wire, a normal pn junction area and a crack position have optical reflectivities different from that of the electrode wire. Thus, the luminance distribution can be binarized with the luminance of the electrode wire and the luminance of the area excluding the electrode wire.

Figure 11:
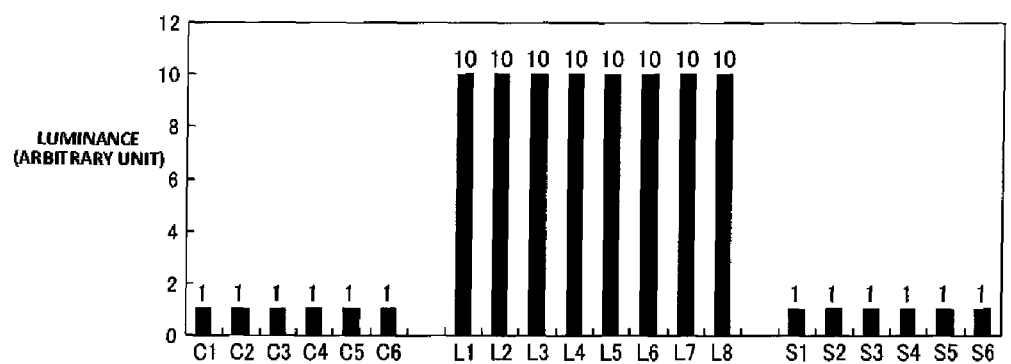
FIG. 11 is a graph illustrating binarized reflection image data as a result of binarization of the luminance distribution illustrated in FIG. 10.

FIG. 11 illustrates an example in which the luminance distribution illustrated in FIG. 10 is binarized on the basis of the ratio "luminance of the electrode wire:the luminance of the normal pn junction and crack position" defined as 10:1.

The binarized reflection image allows clear distinction between the non-EL area and the area excluding the non-EL area.

The detecting device 42 illustrated in FIG. 9 multiples the luminescence intensity distribution image data and binarized reflection image data at the same positions of the semiconductor substrate 100 to calculate determination values of the corresponding positions of the semiconductor substrate 100. Thus, determination value distribution data representing a distribution of determination values of the semiconductor substrate 100 are created. The creation of the determination value distribution data typically requires luminescence images and reflection images acquired at the same positions on the semiconductor substrate 100.

As already described, the intensity difference image data has a clear difference between data of a normal pn junction area where luminescence is caused and data of a non-EL area containing a crack and an electrode wire. The binarized reflection image data has a clear difference between data of an electrode wire and data of the area excluding the electrode wire. The determination value distribution data calculated by the multiplication of the intensity difference image data and binarized reflection image data has a clear difference between the position of the normal pn junction area and an electrode wire, and a crack position having a crack.

For example, when the intensity difference image data is luminance distribution image data, the created intensity difference image data on the semiconductor substrate 100 allows the identification of a crack position as a position having a luminance lower than the luminance in a normal pn junction area. However, since the electrode wire from which no luminescence is observed also has a low luminance, the comparison in luminance of the intensity difference image data may not allow easy distinction between a crack and an electrode wire.

On the other hand, when the binarized reflection image data is luminance distribution data, the binarized reflection image data has a clear difference between the luminance of the electrode wire and the luminance of the area excluding the electrode wire. For example, the luminance of an electrode wire and the luminance of the area excluding the electrode wire may be defined as 10 and 1, respectively, to create the binarized reflection image data. Thus, the multiplication of the intensity difference image data and the binarized reflection image data raises the determination values on the electrode wire and lowers the determination values on a crack position compared with those on the electrode wire. As a result, with reference to the determination value distribution data, a crack position and the area excluding the crack position can be easily distinguished.

Figure 12:
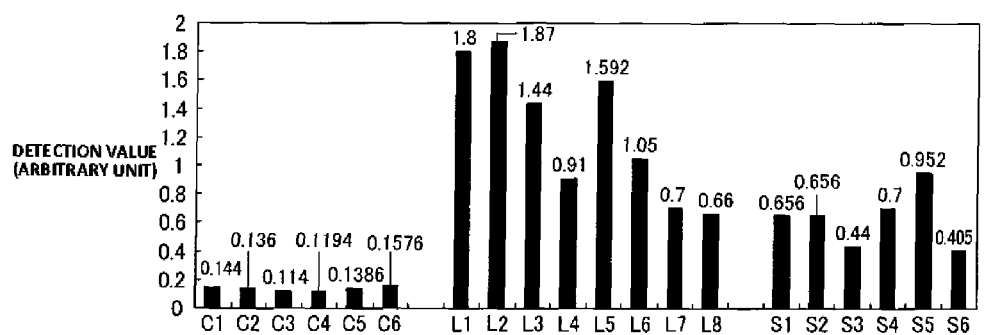
FIG. 12 is a graph illustrating an example of determination values created by a semiconductor examination apparatus according to the second embodiment.

FIG. 12 illustrates a distribution of the determination values calculated by using the luminance distribution of intensity difference image data illustrated in FIG. 6 and the luminance distribution of the binarized reflection image data illustrated in FIG. 11. As illustrated in FIG. 12, determination value distribution data can be acquired which has higher determination values of the non-EL areas L1 to L8 and relatively emphasizes the dark part at the crack positions C1 to C6 only.

The detecting device 42 detects a position of a crack occurring in a semiconductor area with reference to the determination value distribution data. In the example of the determination values illustrated in FIG. 12, there is a difference of at least 2.57 times between the determination values of the crack positions C1 to C6 and of the normal pn junction areas S1 to S6. Since, in this way, there is a large difference of the determination value distribution data between the determination values of a crack position and the area excluding the crack position, the position having a lower determination value may be detected as a crack position.

Figure 13:
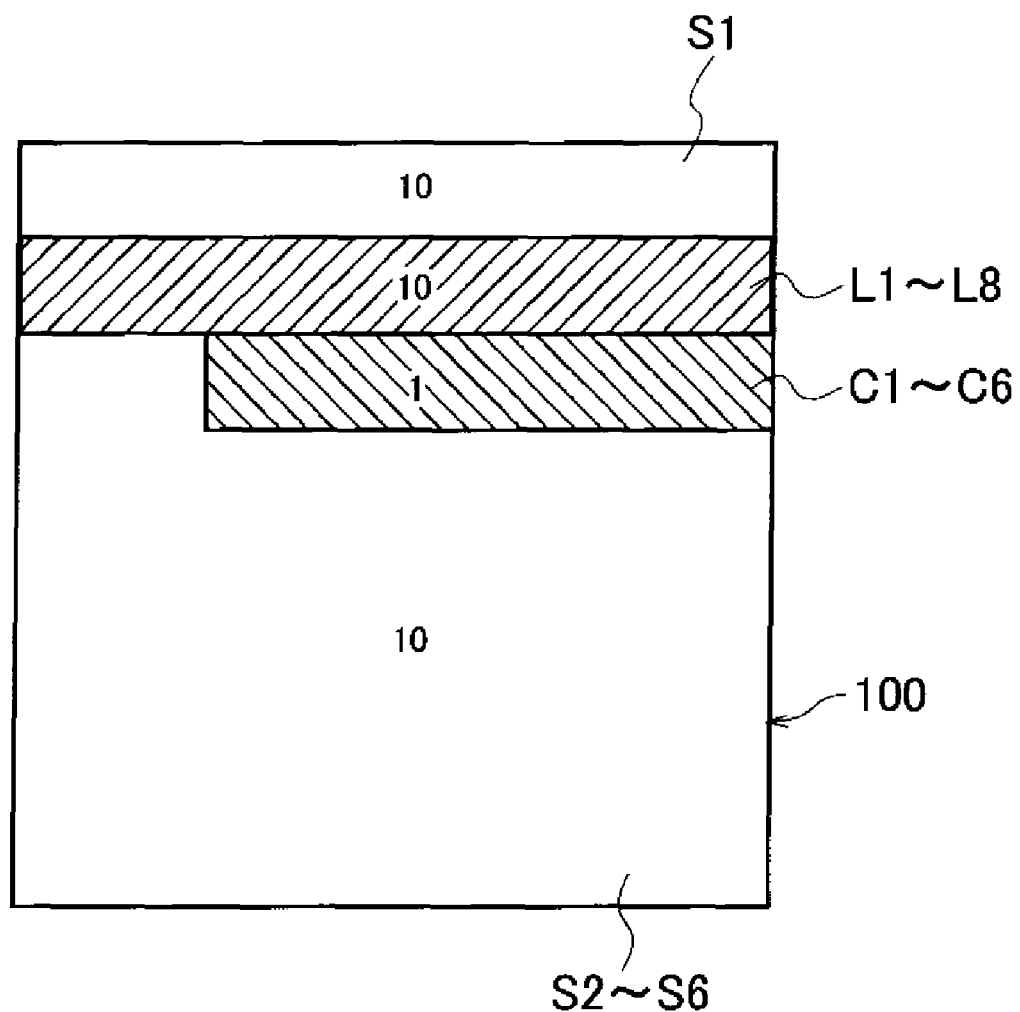
FIG. 13 is a schematic diagram illustrating an example of a determination value distribution image created by a semiconductor examination apparatus according to the second embodiment.

Furthermore, since there is a large difference between the determination values of a crack position and the area excluding the crack position, the determination values may be binarized. This further allows easy detection of a crack position. FIG. 13 illustrates an example of the determination value distribution image acquired by binarization of the determination values illustrated in FIG. 12. Here, on the basis of the ratio "determination value on a crack position:determination value on the area excluding the crack position" defined as 1:10, the determination values are binarized.

As described above, a semiconductor examination apparatus according to the second embodiment multiplies the intensity difference image data indicating positions where luminescence is not observed but having an unclear difference between a crack and a non-EL area containing an electrode wire, for example, and the binarized reflection image data having a clear difference between the non-EL area and the area excluding the non-EL area to calculate the determination values on the corresponding positions of the semiconductor substrate 100. This can clarify the difference between the determination values of a normal pn junction area and non-EL area and the determination values of a crack position. In other words, a crack position and an electrode wire can be distinguished. Thus, the semiconductor examination apparatus according to the second embodiment can implement an inexpensive semiconductor examination apparatus that can detect the position and/or length of a crack with high precision from luminescence images of the semiconductor substrate 100.

The semiconductor examination apparatus according to the second embodiment can easily detect the position and/or length of a crack even when the crack occurs close to an electrode wire on a semiconductor substrate, such as a solar cell substrate, having the electrode wire on its surface, for example.

The other configuration of the second embodiment is substantially similar to that of the first embodiment, and the repetitive description will be omitted. The image capturing device 30 may only be required to have a performance capable of acquiring a reflection image having a difference between a semiconductor area and a non-EL area containing an electrode, for example, that is clear enough for binarization.

Figure 14:
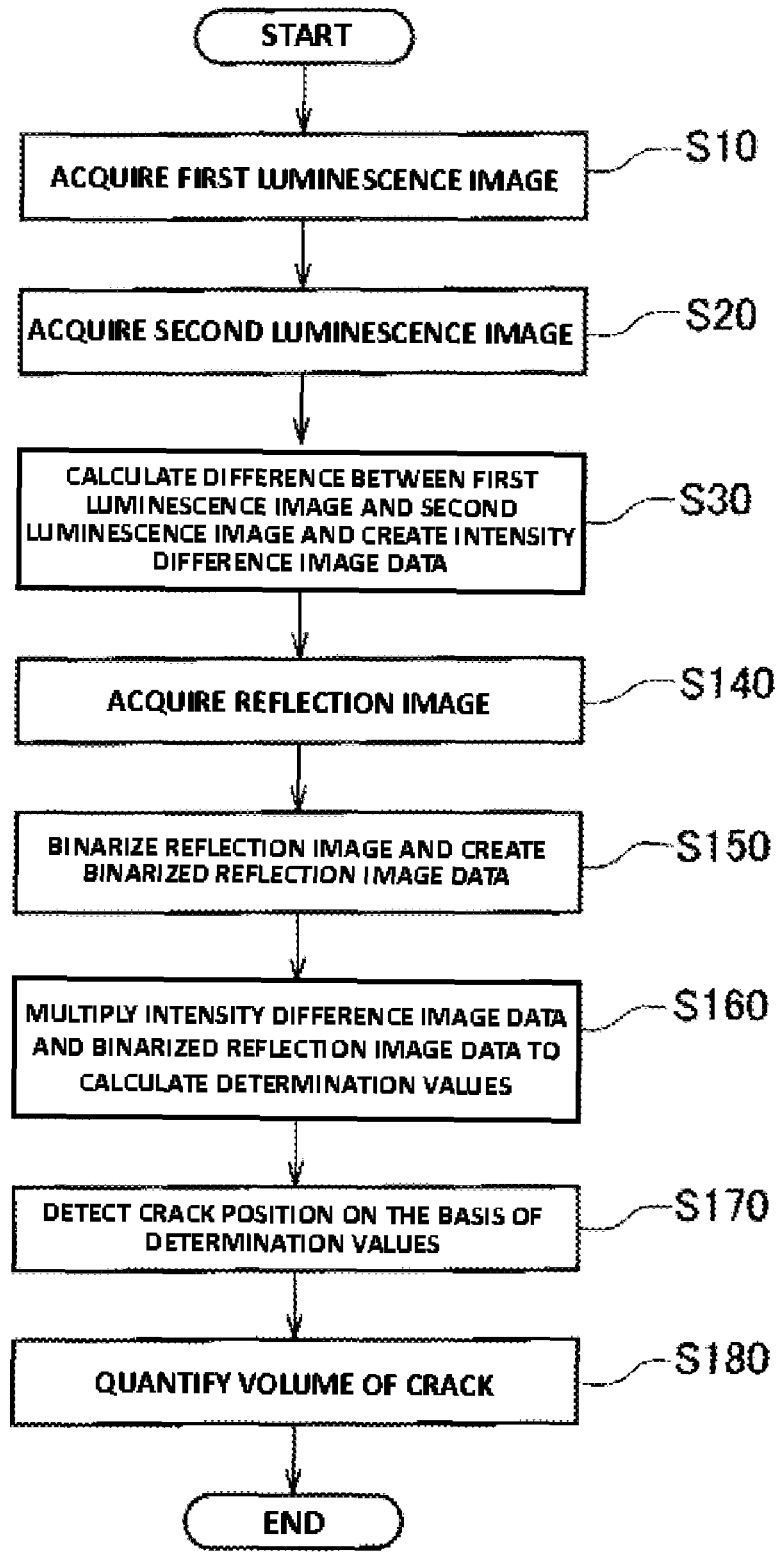
FIG. 14 is a flowchart illustrating a semiconductor examination method according to the second embodiment.

An example of a method for examining the semiconductor substrate 100 by using the semiconductor examination apparatus illustrated in FIG. 9 will be described with reference to the flowchart illustrated in FIG. 14. In the example, the semiconductor substrate 100 is a solar cell substrate. In this case, the non-EL area includes an electrode wire.

Similar to steps S10 to S30 on the flowchart illustrated in FIG. 8, the differences in intensity at the same positions of the first luminescence image and second luminescence image are calculated, and the intensity difference image data of the semiconductor substrate 100 is created. The created intensity difference image data is stored in the recording device 400.

After the supply of the excitation energy Er to the semiconductor substrate 100 is terminated, the projecting device 20 projects the projection energy Ep to the semiconductor substrate 100 in step S140. Thus, the image capturing device 30 acquires the reflection image of the semiconductor substrate 100 where EL is not caused.

It is noted here that the reflection image is acquired at the same position as the position where the luminescence image has been acquired. The acquired reflection image is transmitted to the image data processing unit 40 and is stored as two-dimensional array data in the recording device 400. For example, light may be projected to a solar cell substrate, and a luminance distribution image having a luminance distribution as illustrated in FIG. 10 is acquired as the reflection image. The wavelength and intensity of light to be projected by the projecting device 20 and the angle of the projected light are preferably selected for a larger difference in luminance between the area including an electrode wire and the area excluding the electrode wire.

In step S150, the reflection image processing device 44 binarizes the reflection image read from the recording device 400 to create the binarized reflection image data of the semiconductor substrate 100. For example, the luminance distribution illustrated in FIG. 10 may be binarized to create the binarized reflection image data as illustrated in FIG. 11. The binarized reflection image data is stored in the recording device 400.

In step S160, the detecting device 42 multiplies the intensity difference image data and binarized reflection image data read from the recording device 400 to calculate the determination values of the corresponding positions of the semiconductor substrate 100. The calculated determination values are stored in the recording device 400. For example, the intensity difference image data illustrated in FIG. 6 and the binarized reflection image data illustrated in FIG. 11 may be used to calculate the distribution of the determination values illustrated in FIG. 12.

In step S170, on the basis of the determination values read from the recording device 400, the detecting device 42 detects a crack position having a crack on the semiconductor substrate 100. The data on the detected crack position is stored in the recording device 400. For example, with reference to the distribution of the determination values illustrated in FIG. 12, a position having a lower determination value may be detected as a crack position having a crack. In this case, the data on binarized determination values may be referred to and a crack position is detected.

In step S180, the quantifying device 43 reads data of the crack position from the recording device 400. The quantifying device 43 counts the number of pixels contained in the crack position and quantifies the total sum of the number of pixels as the volume of crack. The volume of crack is stored in the recording device 400.

An operator of the semiconductor examination apparatus may easily check, on the display device 50, the crack position of the determination value distribution image as illustrated in FIG. 13 as a result of the binarization of determination values, for example. The quantified volume of the crack may be displayed on the display device 50.

As described above, according to a semiconductor examination method using the semiconductor examination apparatus of the second embodiment, the luminescence intensity distribution image data and the binarized reflection image data are multiplied to calculate the determination values of corresponding positions of the semiconductor substrate 100. As a result, an inexpensive semiconductor examination method can be implemented that can detect the position and/or length of an occurring crack with high precision from luminescence images of the semiconductor substrate 100.

Having described the first and second embodiments disclosed herein, it is to be understood that the descriptions and drawings included in the present disclosure do not limit the present technological advance. Various alternative embodiments, examples and applicable technologies will be apparent to those skilled in the art from the present disclosure.

Having described examples using electroluminescence in the semiconductor substrate 100, the type of luminescence is not limited to those described. For example, the intensity distribution of heat or electric field caused by the semiconductor substrate 100 receiving excitation energy may be acquired.

It will be obvious that the present invention includes various embodiments and the like not described herein. Accordingly, the technological scope of the present invention is solely determined by matters for restricting the invention according to the appended claims that are valid from the descriptions above.

The invention claimed is:

1. A semiconductor examination apparatus comprising:
an energy source device configured to supply a semiconductor substrate with excitation energy to cause luminescence in the semiconductor substrate;
an image capturing device configured to capture a first luminescence image of the semiconductor substrate when supplied with a first excitation energy and to capture a second luminescence image of the semiconductor substrate when supplied with a second excitation energy that is different in magnitude from the first excitation energy;
a projecting device configured to project a projection energy to be absorbed or reflected at different ratios by a semiconductor area and an area excluding the semiconductor area of the semiconductor substrate where luminescence is not caused;
a luminescence image processing device configured to calculate a difference in luminescence intensity between the first luminescence image and the second luminescence image and generate intensity difference image data;
a reflection image processing device configured to binarize a reflection image of the semiconductor substrate acquired by the image capturing device as a result of the projection of the projection energy to the semiconductor substrate to create binarized reflection image data; and
a detecting device configured to-detect a crack position of a crack occurring in the semiconductor substrate on the basis of the intensity difference image data and the binarized reflection image data.

2. The semiconductor examination apparatus according to claim 1,
wherein the detecting device is further configured to multiply the intensity difference image data and the binarized reflection image data to calculate determination values that are based on the magnitude of the difference of the intensity difference image data on corresponding positions on the semiconductor substrate and detect the crack position on the basis of the determination values.

3. The semiconductor examination apparatus according to claim 2, wherein the detecting device binarizes the determination values and detects the crack position.

4. The semiconductor examination apparatus according to claim 1, wherein the projecting device projects light as the projection energy to the semiconductor substrate.

5. The semiconductor examination apparatus according to claim 1 further comprising a quantifying device configured to quantify a volume of the crack with a number of pixels contained at the crack position.

6. The semiconductor examination apparatus according to claim 1, wherein the energy source device applies current or voltage to supply the excitation energy to the semiconductor substrate.

7. The semiconductor examination apparatus according to claim 1, wherein the intensity difference image data and the binarized reflection image data are luminance distribution image data.

8. The semiconductor examination apparatus according to claim 1, wherein the semiconductor substrate is a solar cell substrate.

9. A semiconductor examination method comprising:
supplying first excitation energy to a semiconductor substrate having a pn junction and acquiring a first luminescence image of the semiconductor substrate;
supplying second excitation energy that is different in magnitude from the first excitation energy to the semiconductor substrate and acquiring a second luminescence image of the semiconductor substrate;
calculating the difference in luminescence intensity between the first luminescence image and the second luminescence image at positions on the semiconductor substrate and generating intensity difference image data;
projecting energy to the semiconductor substrate such that the projected energy is either absorbed or reflected at different ratios by a semiconductor area and an area excluding the semiconductor area of the semiconductor substrate where luminescence is not caused;
acquiring a reflection image of the semiconductor substrate, wherein the reflection image results from the projected energy to the semiconductor substrate;
binarizing the reflection image of the semiconductor substrate to create binarized reflection image data; and
detecting a crack position of a crack occurring in the semiconductor substrate on the basis of the intensity difference image data and the binarized reflection image data.

10. The semiconductor examination method according to claim 9, further comprising:
multiplying the intensity difference image data and the binarized reflection image data to calculate determination values of corresponding positions on the semiconductor substrate that are based on the magnitude of the difference of the intensity difference image data, wherein the crack position is detected on the basis of the determination values.

11. The semiconductor examination method according to claim 10, wherein the determination values are binarized to detect the crack position.

12. The semiconductor examination method according to claim 9, wherein light is projected to the semiconductor substrate to acquire the reflection image.

13. The semiconductor examination method according to claim 9, further comprising quantifying a volume of the crack with a number of pixels contained at the crack position.

14. The semiconductor examination method according to claim 9, wherein current or voltage is applied to supply the excitation energy to the semiconductor substrate.

15. The semiconductor examination method according to claim 9, wherein the intensity difference image data and the binarized reflection image data are luminance distribution image data.

16. The semiconductor examination method according to claim 9, wherein the semiconductor substrate is a solar cell substrate.

17. A semiconductor examination system comprising:
a semiconductor substrate; and
a device for detecting one or more cracks in the semiconductor substrate, the device comprising:
an energy source configured to supply the semiconductor substrate with excitation energy to cause luminescence in the semiconductor substrate;
an image capturing device configured to capture a first luminescence image of the semiconductor substrate when supplied with a first excitation energy and configured to capture a second luminescence image of the semiconductor substrate when supplied with a second excitation energy that is different in magnitude from the first excitation energy;
a luminescence image processing device configured to calculate a difference in luminescence intensity between the first luminescence image and the second luminescence image at corresponding positions on the semiconductor substrate and configured to generate intensity difference image data;
a projecting device configured to project energy to the semiconductor substrate such that the projected energy is either absorbed or reflected at different ratios by a semiconductor area and an area excluding the semiconductor area of the semiconductor substrate where luminescence is not caused;
a reflection image processing device configured to binarize a reflection image of the semiconductor substrate acquired by the image capturing device as a result of the projection of the projection energy to the semiconductor substrate to create binarized reflection image data,
a detecting device configured to detect a crack position of the one or more cracks occurring in the semiconductor substrate on the basis of the intensity difference image data and the binarized reflection image data.

18. The semiconductor examination system according to claim 17,
wherein the detecting device is further configured to multiply the intensity difference image data and the binarized reflection image data to calculate determination values that are based on the magnitude of the difference of the intensity difference image data on corresponding positions on the semiconductor substrate and detect the crack position on the basis of the determination values.

19. The semiconductor examination system according to claim 18, wherein the projecting device projects light as the projection energy to the semiconductor substrate.

20. The semiconductor examination system according to claim 18 wherein the detecting device binarizes the determination values and detects the crack position.

* * * * *